United States Patent
Jacobs et al.

(10) Patent No.: US 10,586,753 B2
(45) Date of Patent: Mar. 10, 2020

(54) IC DIE, ULTRASOUND PROBE, ULTRASONIC DIAGNOSTIC SYSTEM AND METHOD

(71) Applicant: KONINKLIJKE PHILIPS N.V., Eindhoven (NL)

(72) Inventors: Egbertus Reinier Jacobs, Overloon (NL); Johannes Wilhelmus Weekamp, Beek en Donk (NL); Niels Cornelis Wilhelmus Johannes Rijkers, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 614 days.

(21) Appl. No.: 15/300,307

(22) PCT Filed: Mar. 31, 2015

(86) PCT No.: PCT/EP2015/057030
§ 371 (c)(1),
(2) Date: Sep. 29, 2016

(87) PCT Pub. No.: WO2015/150385
PCT Pub. Date: Oct. 8, 2015

(65) Prior Publication Data
US 2017/0136496 A1  May 18, 2017

(30) Foreign Application Priority Data

Mar. 31, 2014 (EP) .................................... 14162615

(51) Int. Cl.
*H01L 23/482* (2006.01)
*A61B 8/12* (2006.01)
(Continued)

(52) U.S. Cl.
CPC ............ *H01L 23/4821* (2013.01); *A61B 8/12* (2013.01); *A61B 8/445* (2013.01); *A61B 8/4494* (2013.01);
(Continued)

(58) Field of Classification Search
CPC ... H01L 23/041; H01L 23/053; H01L 23/055; H01L 23/057; H01L 23/481;
(Continued)

(56) References Cited

U.S. PATENT DOCUMENTS

| 3,747,202 A | 7/1973 | Jordan |
| 6,650,004 B1 | 11/2003 | Horie et al. |

(Continued)

FOREIGN PATENT DOCUMENTS

| EP | 0901164 A2 | 10/1999 |
| WO | 9015438 A1 | 12/1990 |
| WO | 2013057642 A1 | 4/2013 |

*Primary Examiner* — Scott B Geyer

(57) ABSTRACT

An integrated circuit (IC) die (100) is disclosed having a major surface delimited by at least one edge (102) of the IC die, said major surface carrying a plurality of electrically conductive contact plates (130) extending from said major surface beyond the at least one edge such that each contact plate includes an exposed contact surface portion (132) delimited by the at least one edge for mating with an electrically conductive further contact surface portion (230) on at least one further edge (220) of a body (200), said at least one further edge delimiting a cavity for receiving the IC die. An ultrasound probe including such an IC die and a method of providing such an IC die with contacts are also disclosed.

10 Claims, 9 Drawing Sheets

(51) Int. Cl.
- *A61B 8/00* (2006.01)
- *H01L 23/28* (2006.01)
- *H01L 23/00* (2006.01)
- *H01L 23/04* (2006.01)
- *H01L 23/48* (2006.01)
- *B06B 1/02* (2006.01)
- *H01L 21/78* (2006.01)
- *H02N 1/00* (2006.01)
- *H05K 1/18* (2006.01)
- *H01L 41/047* (2006.01)

(52) U.S. Cl.
CPC ............ *B06B 1/0292* (2013.01); *H01L 21/78* (2013.01); *H01L 23/041* (2013.01); *H01L 23/28* (2013.01); *H01L 23/481* (2013.01); *H01L 23/4822* (2013.01); *H01L 24/01* (2013.01); *H01L 24/03* (2013.01); *H01L 24/06* (2013.01); *H02N 1/006* (2013.01); *H05K 1/181* (2013.01); *H01L 41/0475* (2013.01); *H01L 2224/0345* (2013.01); *H01L 2224/0362* (2013.01); *H01L 2224/03462* (2013.01); *H01L 2224/03464* (2013.01); *H01L 2224/05005* (2013.01); *H01L 2224/05147* (2013.01); *H01L 2224/05155* (2013.01); *H01L 2224/05166* (2013.01); *H01L 2224/05171* (2013.01); *H01L 2924/14* (2013.01); *H01L 2924/1433* (2013.01); *H01L 2924/19105* (2013.01); *H01L 2924/2064* (2013.01); *H01L 2924/20641* (2013.01); *H05K 2201/10151* (2013.01)

(58) Field of Classification Search
CPC ............. H01L 23/4821; H01L 23/4822; H01L 23/492; H01L 41/047–0478; H01L 41/053; H01L 2224/41–41505
See application file for complete search history.

(56) References Cited

U.S. PATENT DOCUMENTS

| | | |
|---|---|---|
| 2004/0227595 A1 | 11/2004 | Nguyen et al. |
| 2006/0075818 A1 | 4/2006 | Huang et al. |
| 2007/0167812 A1 | 7/2007 | Lemmerhirt et al. |
| 2008/0203556 A1 | 8/2008 | Huang |
| 2010/0255623 A1 | 10/2010 | Huang |
| 2010/0307786 A1 | 12/2010 | Kohl et al. |
| 2011/0213592 A1 | 9/2011 | Adachi et al. |
| 2011/0300487 A1 | 12/2011 | Marion et al. |
| 2012/0092127 A1 | 4/2012 | Ganapathi et al. |

# IC DIE, ULTRASOUND PROBE, ULTRASONIC DIAGNOSTIC SYSTEM AND METHOD

RELATED APPLICATIONS

This application is the U.S. National Phase application under 35 U.S.C. § 371 of International Application No. PCT/EP2015/057030, filed on Mar. 31, 2015, which claims the benefit of European Application Serial No. 14162615.0, filed Mar. 31, 2014. These applications are hereby incorporated by reference herein.

FIELD OF THE INVENTION

The present invention relates to an integrated circuit (IC) die carrying a plurality of contacts, such as an IC die comprising an ultrasound sensing area.

The present invention further relates to an ultrasound probe including a tip comprising such an IC die.

The present invention further relates to an ultrasonic diagnostic system including such an ultrasound probe.

The present invention yet further relates to a method of providing contacts to such an IC die.

BACKGROUND OF THE INVENTION

ICs find application in a plethora of application domains. The ICs are typically provided in the form of dies or chips that may be mounted on some carrier such as a printed circuit board, in which the electrical connections between the IC die and the carrier may be provided in any suitable manner, for instance using bond wires, ball grid arrays and so on. In most application domains, the nature of the electrical connections is not particularly critical, as the IC die is usually packaged and protected from the outside world, and the dimensions of the IC die, carrier and electrical connections therebetween exhibit a large degree of design freedom.

IC dies are increasingly becoming multifunctional, for instance IC dies may comprise sensing functionality which may be utilized in a wide variety of different devices. An example is provided in US 2012/0092127 A1 in which a IC die including sensor functionality is included in a mobile phone for providing handwriting and fingerprint recognition. As the IC die is embedded in the mobile phone. In an embodiment in this prior art citation, a flexible upper substrate of a combined sensor device as a platform for direct attachment of one or ICs including but not limited to ASICs is provided. The flexible upper substrate including sensing wires and routing leads may be wrapped around the edge of a lower substrate, with the wrapped around edge carrying one or more ICs, such that the ICs are located in between the lower substrate and the upper substrate, thus facilitating a minimal edge border on the device and the glass cover plate extending to the edge of the mobile phone.

However, in certain application domains the particular nature of the electrical connections between the IC die and its carrier is more critical. For instance, IC dies including ultrasound sensing capabilities are increasingly used as a sensing tip of an ultrasound probe such as an ultrasound catheter, in which the electrical interconnections between the IC die and a body of the ultrasound probe are relatively exposed and therefore more vulnerable to damage.

A non-limiting example of an IC die including ultrasound sensing capability is a capacitive micro-machined ultrasonic transducer (CMUT) device. CMUT devices are increasingly popular because CMUT devices can offer excellent bandwidth and acoustic impedance characteristics, which makes them the preferable over e.g. piezoelectric transducers. Vibration of the CMUT membrane can be triggered by applying pressure (for example using ultrasound) or can be induced electrically. Electrical connection to the CMUT device, often by means of an integrated circuit (IC) such as an application specific integrated circuit (ASIC) facilitates both transmission and reception modes of the device. In reception mode, changes in the membrane position cause changes in electrical capacitance, which can be registered electronically. In transmission mode, applying an electrical signal causes vibration of the membrane.

CMUT devices generally operate with a biasing voltage applied. The CMUT can be operated in so called collapsed mode where the biasing voltage applied is increased above the collapse voltage to restrict the membrane and confine part of it against the substrate. The frequency of operation of the CMUT device is characterised by the material and physical properties of the membrane, such as the stiffness, and the size of the cavity. The bias voltage and application of the CMUT device also influence the operation mode. A pressure causes a deflection of the membrane that is electronically sensed as a change of capacitance. A pressure reading can then be derived.

The electrical interconnections between IC die and the body of the ultrasound probe may be provided using bond wires, but bond wires are relatively fragile and may hamper or even prevent the homogeneous application of a lens material, sometimes referred to as the acoustical window, to the sensing area of the IC die, as care has to be taken that the bond wires are not damaged during this application process. In addition, the height of this lens material is typically governed by the required minimum pitch of the bond wires, which may compromise sensitivity of the probe and may increase the overall dimensions of the cross-section of the probe tip, as the bond wires typically bend around the outer edge(s) of the IC die. This may hamper the formation of compact ultrasound probes, e.g. catheters, for use in environments where such compact probes are a necessity, e.g. cardiac investigations.

SUMMARY OF THE INVENTION

The present invention seeks to provide an IC die having robust contacts that facilitate integration of the IC die in a receiving volume such as the cavity of an ultrasound probe.

The present invention further seeks to provide an ultrasound probe including such an IC die.

The present invention yet further seeks to provide a method of providing an IC die with robust contacts.

According to an aspect, there is provided an IC die having a major surface delimited by at least one edge of the IC die, said major surface carrying a plurality of electrically conductive contact plates extending from said major surface beyond the at least one edge such that each contact plate includes an exposed contact surface portion delimited by the at least one edge for mating with an electrically conductive further contact surface portion on at least one further edge of a body, said at least one further edge delimiting a cavity for receiving the IC die.

By providing contact plates that extend beyond the boundary or edge of the IC die, a robust contact can be achieved by the bottom portion of the contact plate, i.e. the contact surface portion delimited by the at least one edge and a receiving surface intended to surround the IC die, such as at least one further edge of a body that delimits a cavity for receiving the IC die. Not only does this provide a straightforward manner of establishing electrical contacts between the IC die and a receiving surface, but it furthermore ensures that the contacts emanating from the major surface of the IC die are substantially flat, thereby facilitating the homogeneous deposition of a lens material onto the major surface if required.

This is in a particular relevant if the major surface further comprises an ultrasound sensing area, as in such an embodiment the image forming capability of the ultrasound sensing area may improve because of the improved homogeneity of the lens material, which may be formed at a reduced thickness, thereby improving sensitivity of the IC die.

In an embodiment, the ultrasound sensing area is defined by a plurality of capacitive micromachined ultrasonic transducer (CMUT) elements. This has the advantage of facilitating a particularly sensitive ultrasound sensing area as a homogeneous lens material can be easily formed to a relatively modest thickness.

The major surface may comprise a plurality of bond pads, wherein each electrically conductive contact plate extends from one of said bond pads. For instance, the electrically conductive contact plates may be plated onto the bond pads. Alternatively, the electrically conductive contact plates may be formed in trenches extending from the bond pads, e.g. by plating, which has the advantage that the major surface of the IC die may be flush, i.e. the contact plates lie in the major surface rather than are formed on top of the major surface.

The electrically conductive contact plates may be made of a metal or metal alloy. In some embodiments, the metal or metal alloy may be diamagnetic in order to facilitate the use of the IC die in magnetic devices such as magnetic resonance imaging devices. For instance, the diamagnetic metal may be copper or nickel or any other suitable diamagnetic metal.

The contact plates preferably have a thickness of at least 20 micron, at least 50 micron or even at least 100 micron to substantially increase the robustness of the contact plates, thereby further preventing the electrically conductive contact plates from being damaged during mounting the IC die onto its receiving body or during use of the IC die.

In an embodiment, the IC die comprises a single continuous edge. For instance, the IC die may be a circular die.

According to a further aspect, there is provided an ultrasound probe comprising a tip including the IC die including an ultrasound sensing area according to one of the above embodiments; and a body having at least one further edge delimiting a cavity comprising the IC die, said at least one further edge comprising a plurality of electrically conductive first further contact surfaces, wherein each electrically conductive first further contact surface is conductively coupled to the contact surface portion of one of said contact plates. By providing the contacts between the IC die and the tip body at the contact surface between the electrically conductive contact plates and the one or more body edges, a particularly compact and robust set of contacts is provided, which obviates the need for a relatively thick protective layer over the ultrasound sensing area of the IC die, thereby improving robustness and sensitivity of the ultrasound probe such as a forward looking ultrasound catheter.

Each electrically conductive first further contact surface may be conductively coupled to the contact surface portion of one of said contact plates by a conductive solder or a conductive glue.

In an embodiment, said body comprises a flex foil including a plurality of conductive tracks on the flex foil, wherein each conductive track includes one of said first further contact surfaces. This has the advantage that an ultrasound probe with a particularly small form factor can be provided, which facilitates the use of such probes in challenging areas of a patient's body, such as the heart. This is particularly the case if the IC die has a single continuous edge, e.g. is a circular die.

The tip may further house signal processing circuitry on a printed circuit board carrying a plurality of board contacts conductively coupled to signal processing circuitry inputs; the flex foil comprises an annular section housing the IC die and an arcuate section extending from the annular section, said arcuate section comprising a pair of opposing edge portions each comprising a plurality of electrically conductive second further contact surfaces, each electrically conductive second further contact surface forming part of one of said conductive tracks; and each electrically conductive second further contact surface is conductively coupled to one of said board contacts. This arrangement facilitates the formation of a particularly compact tip.

The tip may be encapsulated in a resin to protect the signal processing circuitry from exposure to the outside world.

According to another aspect, there is provided an ultrasonic diagnostic system comprising an ultrasound probe according to an embodiment of the present invention.

According to yet another aspect, there is provided a method of providing contacts to a IC die, the method comprising providing a wafer comprising a plurality of IC dies, each die comprising a major surface carrying a plurality of electrically conductive contacts, wherein the dies are spatially separated from each other by sacrificial regions; forming electrically conductive contact plates on said respective major surfaces, each of said electrically conductive contact plates extending from one of said electrically conductive contacts into one of said sacrificial regions; and singulating the IC dies by removing said sacrificial regions such that the major surface of each IC die is delimited by at least one edge of the IC die, and wherein the electrically conductive contact plates extend from said major surface beyond the at least one edge such that each contact plate includes an exposed contact surface portion delimited by the at least one edge for mating with an electrically conductive further contact surface on at least one further edge of a body, said at least one further edge delimiting a cavity for receiving the IC die. This provides a plurality of IC dies that can be used in applications in which the IC die is to be placed in a receiving cavity as previously explained.

The step of forming the electrically conductive contact plates on said respective major surfaces may comprise forming the electrically conductive contact plates to a thickness of at least 20 micron by plating an electrically conductive material onto the respective major surfaces in order to obtain a particularly robust set of contact plates.

In an embodiment, the method further comprises forming a plurality of trenches in said respective major surfaces, wherein each trench extends from one of said electrically conductive contacts into one of said sacrificial regions, and wherein the step of forming the electrically conductive contact plates on said respective major surfaces comprises filling said trenches with an electrically conductive material. This has the advantage that an IC die having a substantially flush major surface may be produced.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1A:
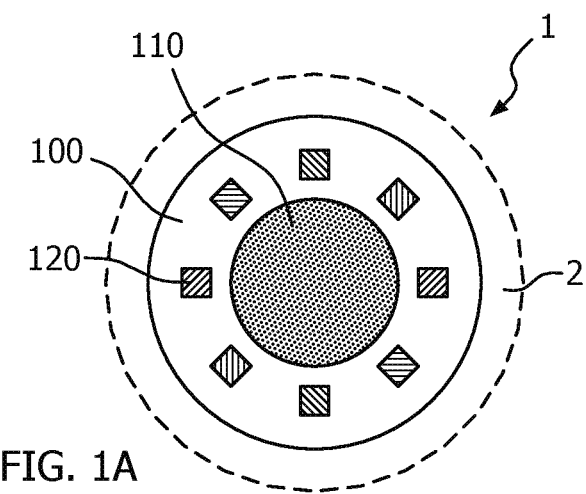
FIGS. 1A-1H schematically depict a method of forming contacts of an IC die according to an embodiment of the present invention.
Figure 1B:
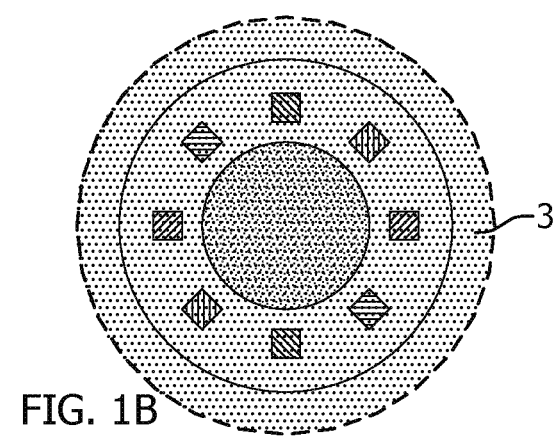

It should be understood that the Figures are merely schematic and are not drawn to scale. It should also be understood that the same reference numerals are used throughout the Figures to indicate the same or similar parts.

FIGS. 1A-1H schematically depict a method of forming contacts of an IC die according to an embodiment of the present invention. The contacts are typically formed when the IC die 100 forms part of a wafer 1, wherein IC dies 100 are separated by a sacrificial portion 2 of the wafer 1. Such a wafer 1 is provided in step FIG. 1A. The wafer 1 may be made of any suitable material or combination of materials and may have any suitable dimension, e.g. a 4 inch, 6 inch, 8 inch diameter and so on. The IC dies 100 on the wafer 1 also may be any suitable IC die including any suitable functionality or circuitry. As should be understood, the nature or embodiment of the IC die 100 is not particularly relevant to at least some aspects of the present invention, as these aspects are simply concerned with the provision of contacts to any type of an IC die 100 having any suitable shape such that the IC die 100 can be mounted in a recess or cavity of a receiving body matching the shape of the IC die 100 as will be explained in more detail below.

In some embodiments, a major surface of the IC die 100 may comprise a central sensing area 110, e.g. an array of ultrasound transducers such as an array of CMUT cells or piezoelectric ultrasound transducers. The manufacture of such sensing arrays is well-known per se and will not be explained in further detail for the sake of brevity. It suffices to say that any suitable central sensing area 110 may be used, which may be provided in any suitable manner. The IC die 100 may have any suitable shape, e.g. a circular shape or a polygonal shape. In some embodiments, the IC die 100 may have a circular shape, for instance if the IC die 100 is to be integrated in an ultrasound probe as will be explained in more detail later.

The IC die 100 typically comprises a plurality of bond pads 120 or other external contacts for providing electrical contacts to the internal circuitry of the IC die 100 in or on a major surface. The bond pads 120 may have any suitable shape and may be located in a peripheral region of the major surface, e.g. surrounding a sensing area 110 such as an ultrasound transducer array, e.g. a CMUT array or a piezoelectric ultrasound sensor array. The bond pads 120 may be made of any suitable electrically conductive material. For instance, in case of a CMOS manufacturing process, the bond pads 120 may be made of silicided polysilicon, copper, aluminium, a copper/aluminium alloy and so on. Copper may be used if the IC die 100 is to be used within a magnetic field, e.g. within the magnetic field of a MRI device, as copper is a diamagnetic metal that only weakly interacts with magnetic fields, such that small amounts of copper or another suitable diamagnetic metal, e.g. nickel or titanium, in such a magnetic field will not substantially interfere with or disrupt the magnetic field.

Only a part of the wafer 1 including a single IC die 100 surrounded by sacrificial wafer portion 2 is shown for the sake of clarity. It should be understood that the wafer 1 typically comprises a plurality of IC dies that are singulated In step FIG. 1B, the major (upper) surface of the wafer 1 is provided with an electrically conductive metal base layer 3 for spreading a current across the surface of the wafer 1 during a subsequent plating step. Any suitable metal or metal alloy may be used for this purpose, such as copper, nickel, titanium or chromium. In some embodiments, the metal base layer 3 is a diamagnetic metal such as copper, nickel or titanium. The metal base layer 3 may be formed in any suitable manner, e.g. through sputtering and/or evaporation, through physical vapour deposition (PVD) and so on. The metal base layer 3 may be omitted if the contacts to be formed are formed using an electroless plating or other metal deposition step. However, electroplating is particularly advantageous if the contacts to be formed have a relatively large thickness, e.g. several tens of microns, such as 20 microns, 50 microns, 100 microns or more, as electroplating is a particularly quick technique for forming metal layers.

Figure 1C:
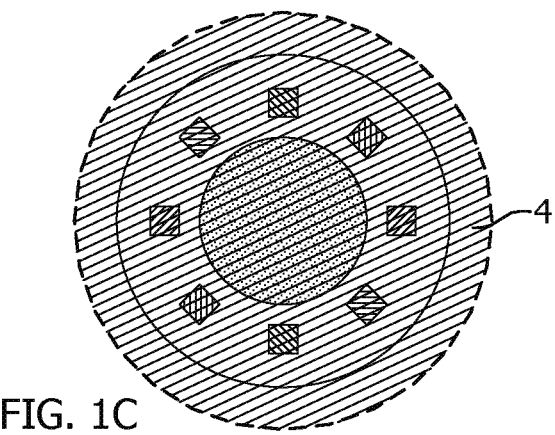

Next, a photoresist layer 4 is formed over the exposed major surface of the wafer 1 as shown in step FIG. 1C, e.g. by spincoating. Any suitable photoresist material may be used, such as polyimide and Novolac although other suitable photoresist materials will be apparent to the skilled person.

Figure 1D:
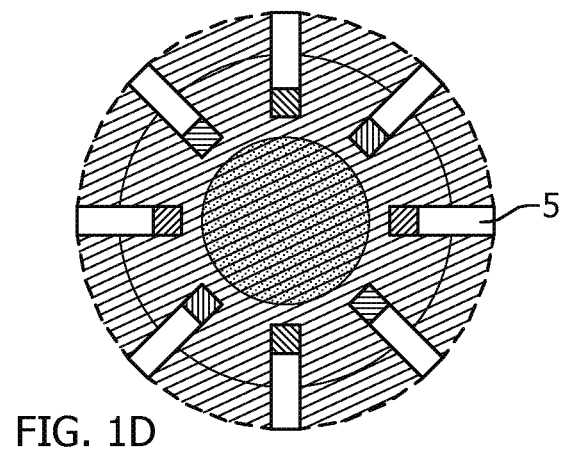

The resist layer 4 is subsequently patterned in step FIG. 1D to form trenches 5 that open up a region over the bond pads 120 and extend from the bond pads 120 into the sacrificial region 2 of the wafer 1. In case the metal base layer 3 is present, the metal base layer 3 is exposed by the trenches 5. Otherwise, the bond pads 120 and regions of the wafer 1 are exposed by the trenches 5. The trenches 5 may be formed in any suitable manner, e.g. by developing the resist layer 4 using UV irradiation through a photo mask (not shown) and removing (un)developed photoresist material, e.g. using a suitable solvent, to form the trenches 5. As this is well-known per se, this will not be explained in more detail for reasons of brevity only.

At this point it is noted that it is equally feasible to replace the photoresist layer 4 with a hard mask layer that is subsequently patterned using suitable etch recipes to form the trenches 5. In this embodiment, the metal base layer 3 may for instance be used as an etch stop layer. Again, as this is well-known per se, this will not be explained in more detail for reasons of brevity only.

Figure 1E:
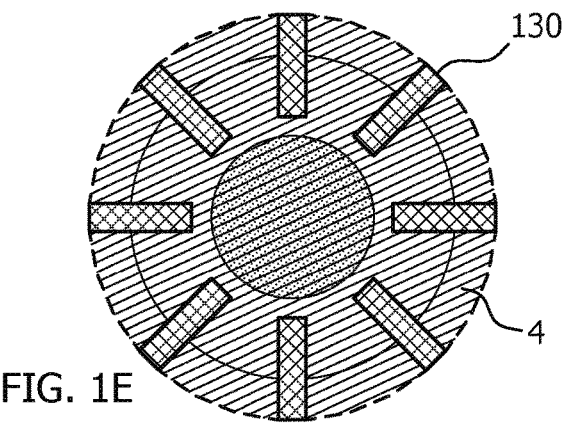

In step FIG. 1E, the trenches 5 are (partially) filled with an electrically conductive material, preferably a metal to form contact plates 130 extending from the bond pads 120 into the sacrificial region 2 of the wafer 1. In some embodiments, the metal is a diamagnetic metal such as copper or nickel for reasons already explained above. The trenches 5 may be filled with the electrically conductive material using any suitable deposition technique, such as electroless plating or electroplating. Electroplating is particularly suitable for forming the contact plates 130 at relatively high speed. This is for instance advantageous if the contact plates 130 are formed to a thickness of several tens of microns, e.g. 50 micron, 100 micron or more.

Figure 1F:
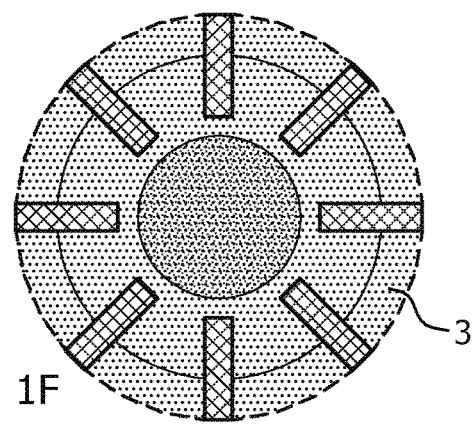

Next, the photoresist layer 4 is stripped from the wafer 1 to expose the metal base layer 3 if present, as shown in step FIG. 1F. Otherwise the wafer 1 is exposed. The photoresist layer 4 may be stripped using any suitable solvent or fluid. Alternatively, in case a hard mask is used instead, the hard mask may be removed at this point, e.g. using a suitable etch recipe terminating on e.g. the metal base layer 3.

Figure 1G:
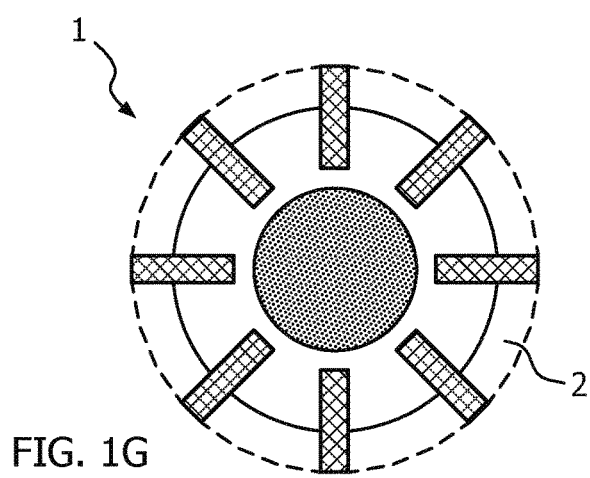

Step FIG. 1G is an optional step that only applies if the metal base layer 3 is present. In this step, the exposed portions of the metal base layer 3 are removed, e.g. using a suitable etch recipe to expose the major surface of the wafer 1 including the sacrificial regions 2. This is necessary because the metal base layer 3 forms an electrical short between the respective contact plates 130. In case the metal base layer 3 is made of a metal that can be selectively removed relative to the contact plates 130, e.g. the metal base layer 3 and the contact plates 130 are made of different metals, the exposed portions of the metal base layer 3 may be removed in a maskless step, i.e. using the contact plates 130 as hard masks. Alternatively, e.g. in case the metal base layer 3 and the contact plates 130 are made of a similar or the same metal, a lithographic mask may be applied to selectively remove the metal base layer 3 outside the areas occupied by the contact plates 130.

Figure 1H:
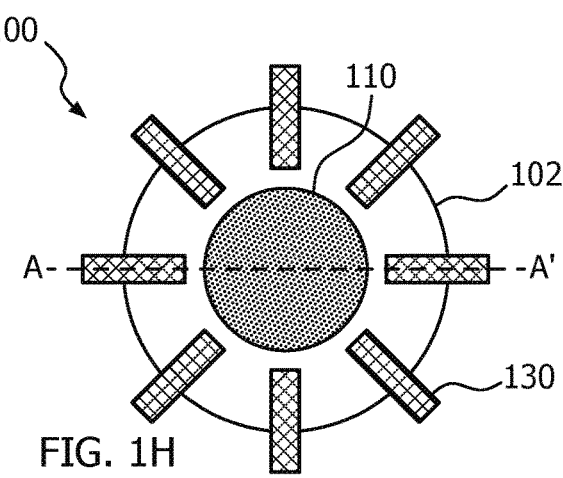

Finally, the IC dies 100 are individualized as shown in step FIG. 1H. To this end, the sacrificial portions 2 of the wafer 1 are selectively removed, e.g. through a backside etching step, which is commonly applied when forming circular IC dies as such die shapes typically cannot be obtained through wafer dicing. As such a wafer backside etching process is well-known per se, this will not be explained in further detail for the sake of brevity only. The resulting IC dies 100 comprise a plurality of contact plates 130 that extend from the bond pads 120 over the edge 102 (or plurality of edges in case of a polygonal IC die).

Figure 2:
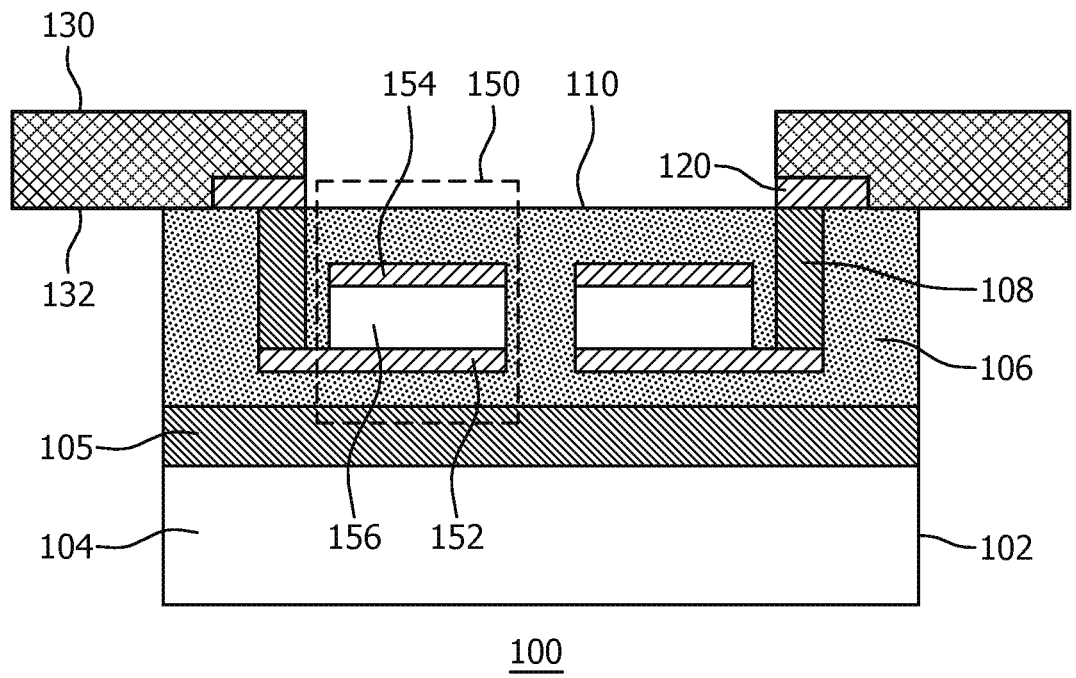
FIG. 2 schematically depict a cross-section of a non-limiting example of an IC die manufactured in accordance with the method of FIGS. 1A-1H.

A cross-section of a non-limiting example embodiment of an IC die 100 along the line A-A' in step FIG. 1H is schematically shown in FIG. 2. The IC die comprises a sensing area 110 here defined by a plurality of CMUT cells 150, each including a first electrode 152 separated from a second electrode 154 by a cavity 156. The first electrode 152 and the second electrode 154 may be made of any suitable conductive material, e.g. a suitable metal or metal alloy including aluminium, copper, nickel and so on. The first electrode 152 and the second electrode 154 may be separated from the cavity 156 by respective electrically insulating layers (not shown), which may comprise any suitable dielectric material, e.g. $SiO_2$, $Si_3N_4$ or the like. The second electrode 154 may be embedded in a membrane of the CMUT cell 150, which membrane may form part of a (patterned) dielectric layer stack 106, which may include one or more layers of suitable dielectric materials, e.g., $SiO_2$, $Si_3N_4$ or the like. It will however be understood that other types of sensor cells, e.g. piezoelectric ultrasound sensor cells, are equally feasible, or that the sensing area 110 may not be present in some embodiments.

The bond pads 120 are typically connected to a conductive structure inside the IC die 100 by conductive interconnects extending through at least a part of the dielectric layer stack 106, e.g. vias 108, which may be made of any suitable electrically conductive material. The IC die 100 typically comprises a substrate 104 which may include circuit elements (not shown), e.g. defining an application specific integrated circuit (ASIC), which circuit elements may be interconnected by a metallization stack (not shown) as is well known per se.

The CMUT cells 150 may be separated from the substrate 104 (and metallization stack) by a passivation and/or planarization layer stack 105, which may be made of any suitable material or combination of materials, e.g. one or more dielectric layers. The vias 108 may extend through the passivation and/or planarization layer stack 105 to connect the bond pads 120 to circuit elements formed on the substrate 104. Alternatively, separate vias (not shown) may be present through the passivation and/or planarization layer stack 105, such that the vias 108 are connected to the circuit elements through these separate vias and the metallization stack.

The metal contact plates 130 extend from the bond pads 120 beyond the edge (or edges) 102 of the IC die 100, such that the metal contact plates 130 include a contact surface portion 132 delimited by the edge(s) 102. This allows for the IC die 100 to be placed in a recess or the like of a body delimited by one or more further edges, such that the majority of the IC die 100 is recessed in this recess whilst the contact surface portions 132 of the contact plates 130 engage with the further edge(s) of this body such that the IC die 100 is suspended in the recess or the like. The body edge(s) typically comprise further contacts for engaging with the contact surface portions 132 of the contact plates 130, as will be explained in more detail below by way of non-limiting example.

It should be understood that FIG. 2 simply gives a non-limiting example of an IC die 100 including an ultrasound sensing area 110. As previously explained, the internal structure or functionality of the IC die 100 is of no particular relevance to at least some embodiments of the present invention, as the inventive concept of these embodiments is to provide contact plates 130 that can support the IC die 100 when it is mounted in a recess or the like with the contact plates 130 engaging with the edge delimiting the recess.

Figure 3:
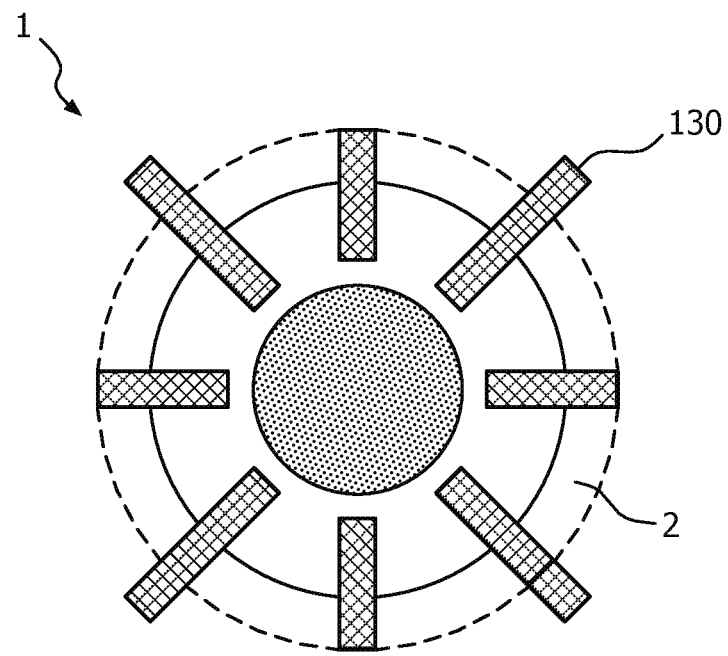
FIG. 3 schematically depicts a variant to a step of the method of FIGS. 1A-H.

In the method of FIGS. 1A-1H, the contact plates 130 are formed to extend into the sacrificial region 2 of the wafer 1 as governed by the dimensions of the trenches 5 that are formed in the resist layer 4. At this point it is noted that some of the trenches 5 may be elongated such that the contact plates 130 formed therein extend beyond the sacrificial region 2 of the wafer 1. This is schematically depicted in FIG. 3. This has the advantage that upon release of the IC die 100 from the wafer 1, e.g. by the aforementioned back etching step, the IC die 100 remains suspended in the wafer 1 by the extended contact plates 130. The IC die 100 may then be released from the wafer 1 in a controlled manner, e.g. by punching or laser cutting the extended contact plates 130.

FIGS. 4A-4F schematically depicts an alternative method for forming the contact plates 130 in which the contact plates 130 are formed in the IC die 100 rather than on top of the major surface of the die as in FIG. 1A-1H. Reference numerals that are the same in both FIGS. 1A-1H and FIGS. 4A-4F have the same meaning as previously described in the detailed description of FIG. 1 such that the features corresponding to these reference numerals will not be explained in detail again for the sake of brevity. As before, the method starts in step FIG. 4A with the provision of a wafer 1, wherein IC dies 100 are separated by a sacrificial portion 2 of the wafer 1. As before, each IC die 100 typically comprises a plurality of bond pads 120 or other external contacts for providing electrical contacts to the internal circuitry of the IC die 100 in or on a major surface. The bond pads 120 may surround a sensing area 110 such as an ultrasound transducer array, e.g. a CMUT array or a piezoelectric ultrasound sensor array.

Figure 4A:
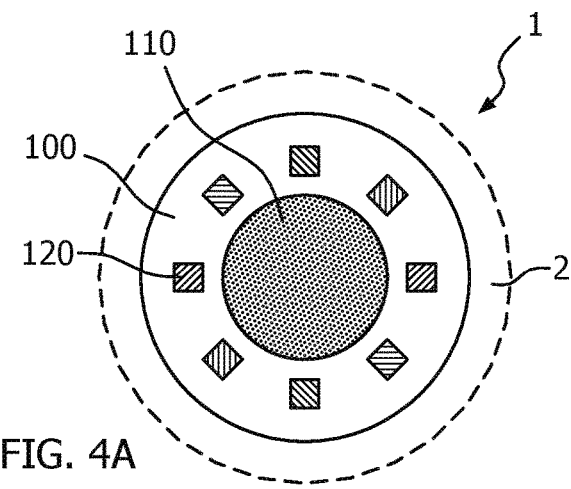
FIGS. 4A-4F schematically depicts a method of forming contacts of an IC die according to another embodiment of the present invention.
Figure 4B:
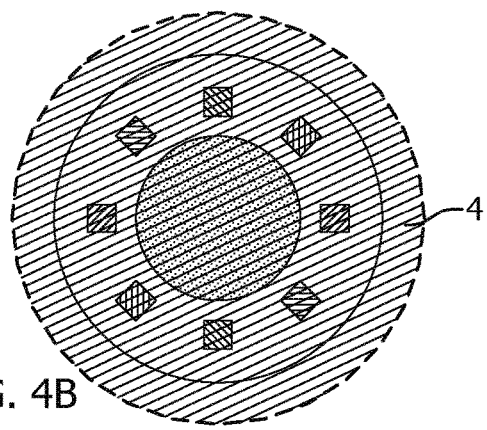
Figure 4C:
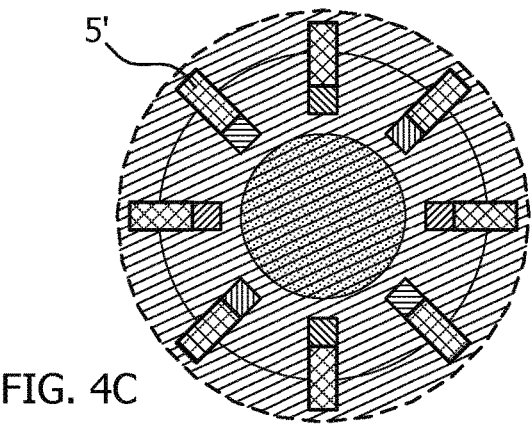
Figure 4D:
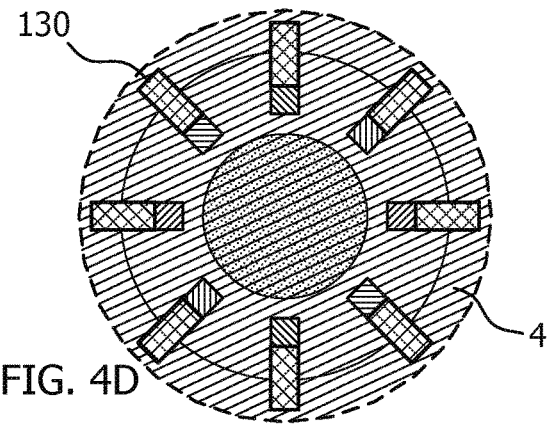
Figure 4E:
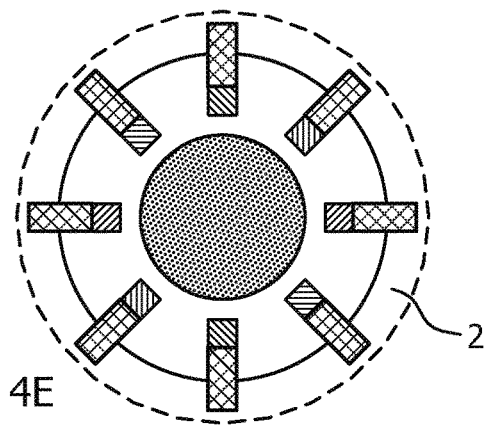

In step FIG. 4B, the photoresist layer 4 is formed over the major surface of the wafer 1 and developed as previously explained. Next in step FIG. 4C, trenches 5' are formed in the areas of the wafer 1 exposed by the developed photoresist layer 4. The trenches 5' may be formed by a suitable etch recipe and each trench 5' typically extends alongside a bond pad 120. The bond pad 120 may be exposed by the patterned photoresist layer 4, i.e. may be exposed to the etch recipe, in case the bond pad 120 is inert to the chosen etch recipe. This has the advantage that the openings in the patterned photoresist layer 4 do not have to be accurately aligned with the respective edges of the bond pads 120. The etch step to form the trenches 5' may terminate on an etch stop layer in the IC die 100. For instance, the passivation and/or planarization stack 106 over the substrate 104 may be used as the etch stop layer. Alternatively, a dedicated etch stop layer may be included in the IC die 100 as is well-known per se.

Next, the trenches 5' are filled by an electrically conductive material, e.g. a metal such as a diamagnetic metal as previously explained, to form the contact plates 130. This is shown in step FIG. 4D. The formation of the contact plates 130 optionally may be preceded by the deposition of the metal base layer 3 at least in the trenches 5'. This is not explicitly shown. The photoresist 4 is subsequently removed in step FIG. 4E and the IC dies 100 are individualized in step FIG. 4F as previously explained to yield IC dies in which the contact plates 130 are flush with the major surface of the IC die 100.

Figure 4F:
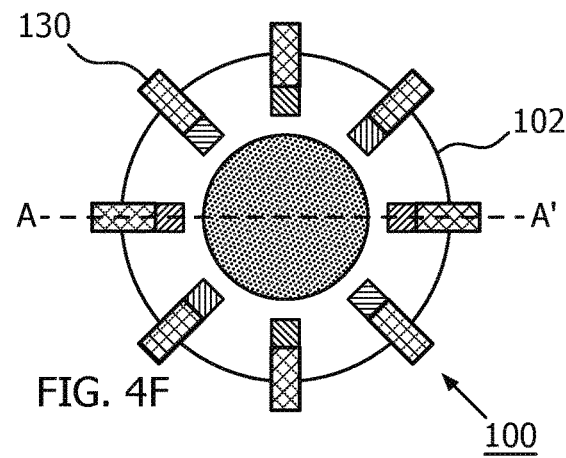
Figure 5:
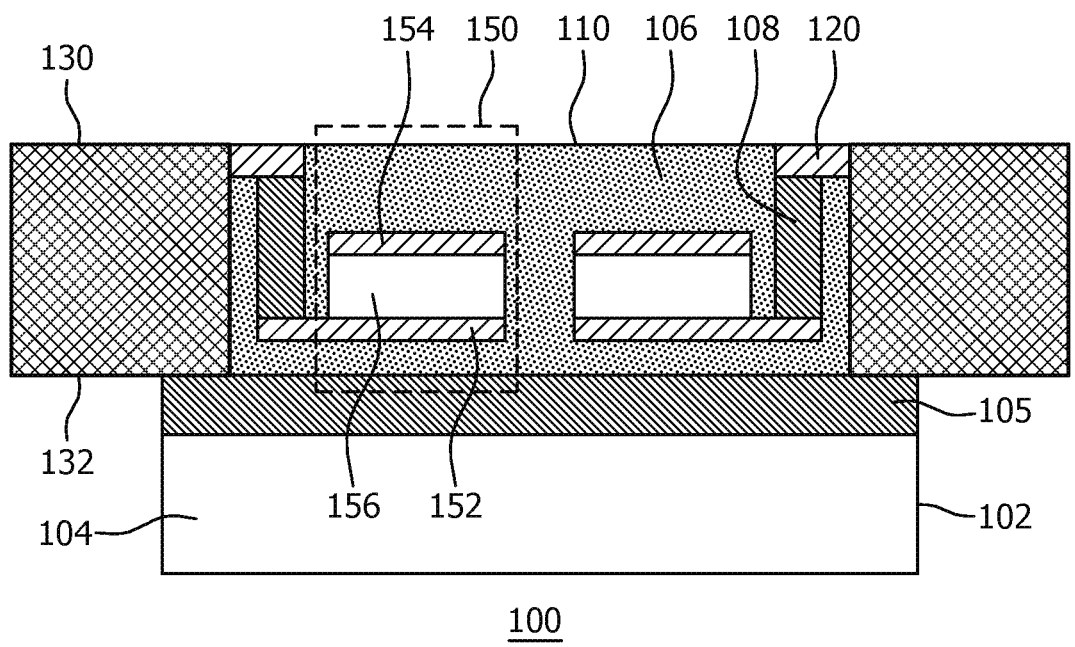
FIG. 5 schematically depicts a cross-section of a non-limiting example of an IC die manufactured in accordance with the method of FIG. 4A-4F.

This is shown in more detail in FIG. 5, which schematically depicts a cross-section of a non-limiting example of an IC die 100 along the line A-A' shown in FIG. 4F. Reference numerals that are the same in both FIG. 2 and FIG. 5 have the same meaning as previously described in the detailed description of FIG. 2 such that the features corresponding to these reference numerals will not be explained in detail again for the sake of brevity. As can be seen, the contact plates 130 are now recessed in the IC die 100 such that the upper surface of the contact plates 130 are flush with the major surface of the IC die 100 including the bond pads 120 and the optional sensing area 110. This allows for the IC die 100 to be mounted in a receiving cavity in a particular flush manner at the expense of less robust contact plates 130, as the thickness of the contact plates 130 is now governed by the thickness of the dielectric layer stack 106, which for instance in case of an IC die 100 comprising a plurality of CMUT cells 150 each having a relatively large membrane diameter of 100 micron or beyond results in a thickness of the dielectric layer stack 106 in the region of 5-10 micron.

In FIG. 5, the metal contact plates 130 extend from a side surface of the bond pads 120 (and underlying via 108 where applicable) beyond the edge (or edges) 102 of the IC die 100, such that the metal contact plates 130 include a contact surface portion 132 delimited by the edge(s) 102. This allows for the IC die 100 to be placed in a recess or the like of a body delimited by one or more further edges, such that the majority of the IC die 100 is recessed in this recess whilst the contact surface portions 132 of the contact plates 130 engage with the further edge(s) of this body such that the IC die 100 is suspended in the recess or the like. The body edge(s) typically comprise further contacts for engaging with the contact surface portions 132 of the contact plates 130, as will be explained in more detail below by way of non-limiting example.

It should be understood that like FIG. 2, FIG. 5 simply gives a non-limiting example of an IC die 100 including an ultrasound sensing area 110. As previously explained, the internal structure or functionality of the IC die 100 is of no particular relevance to at least some embodiments of the present invention, as the inventive concept of these embodiments is to provide contact plates 130 that can support the IC die 100 when it is mounted in a recess or the like with the contact plates 130 engaging with the edge delimiting the recess.

Figure 6:
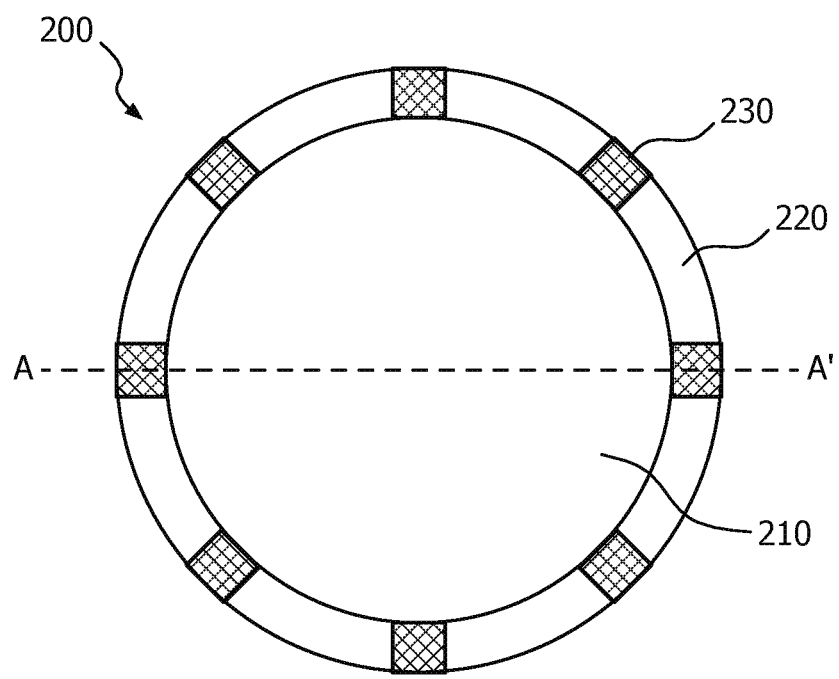
FIG. 6 schematically depicts a top view of an aspect of a body of an ultrasound probe according to an embodiment of the present invention.

FIG. 6 schematically depicts a top view of a body 200 having one or more edges 220 delimiting an opening, e.g. cavity 210 for receiving an IC die 100 according to an embodiment of the present invention. The edge or edges 220 typically carry a plurality of electrically conductive body contact portions 230 that are distributed in a pattern that matches the pattern of the contact plates 130 on the IC die. In other words, the body contact portions 230 are spaced such that they mate with the contact surface portions 132 of the contact plates 130 when the IC die 100 is suspended in the opening or cavity 210.

Figure 7:
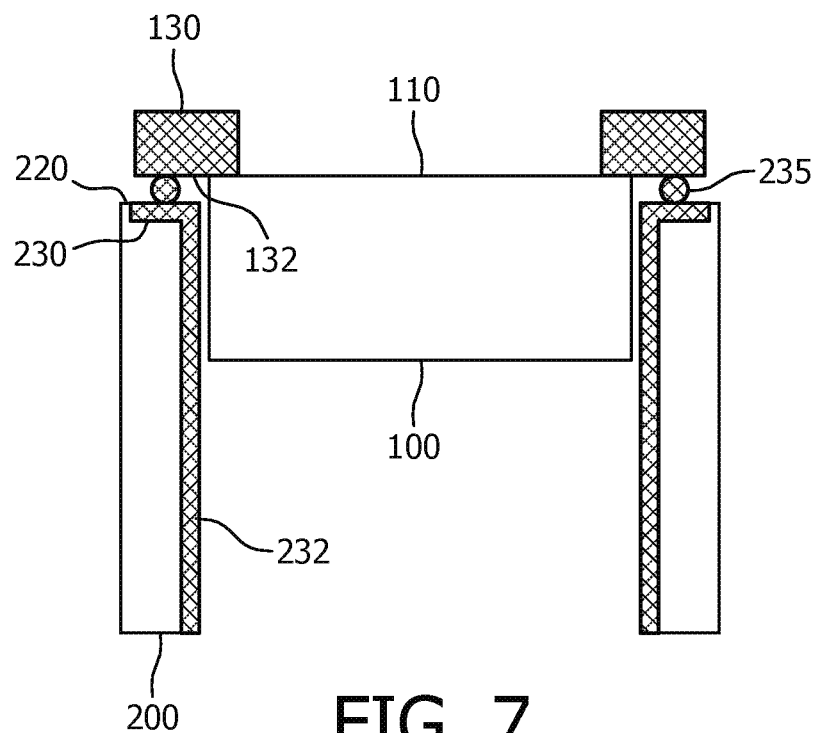
FIG. 7 schematically depicts a cross-section of an aspect of a tip of an ultrasound probe according to an embodiment of the present invention.

FIG. 7 schematically depicts a cross-section along the line A-A' of the body 200 in which the body 200 has received an IC die 100. The body contact portions 230 may be conductively coupled to the contact surface portions 132 of the contact plates 130 using any suitable coupling medium, e.g. an electrically conductive solder or electrically conductive glue. In an embodiment, the body edge(s) 220 may be provided with a preformed solder sheet in order to form the conductive contacts 235, e.g. solder bumps. The contact plates 130 prevent the IC die 100 from falling through the opening 210 because the contact plates 130 rest on the body edge(s) 220.

The thickness of the contact plates 130 may be chosen such that the contact plates 130 are unlikely to be damaged during a device manufacturing process, e.g. during the formation of the conductive contacts 235 or during the packaging of a device including the body 200 and the IC die 100. For instance, if the body 200 forms part, e.g. forms the tip, of an ultrasound probe, the contact plates may have a thickness of several microns, or even several tens of microns, e.g. 50 micron or 100 micron and beyond to ensure that the IC die 100 and its contacts can withstand the stresses to which the IC die 100 is subjected during the manufacturing and packaging of this part of the probe.

In an embodiment, the body contact portions 230 may form part of conductive tracks 232 provided, e.g. embedded, in the body 200, which facilitate connection of the circuitry of the IC die 100 to a further circuit (not shown), e.g. a signal processing circuit for processing signals generated by circuit elements on the IC die. For instance, the conductive tracks 232 may relay signals generated by ultrasound transducer cells, e.g. CMUT cells, in the sensing area of the IC die 100 to a signal processing arrangement conductively coupled to the conductive tracks 232. The conductive tracks 232 and the body contact portions 230 on the body edge(s) 220 may be formed in any suitable manner. In a particular embodiment, the body contact portions 230 are plated onto the body edge(s) 220, e.g. using electroplating or electroless plating.

In a particularly advantageous embodiment, the body 200 may form part of the tip of a forward looking ultrasound probe, such as the tip of a forward looking ultrasonic catheter, in which case the IC die 100 comprises an ultrasound sensing area 110 including an array of transducer cells, e.g. CMUT cells 150 or piezoelectric transducer cells. The transducer cells facilitate forward ultrasound imaging when the IC die 100 is mounted on the tip of the ultrasound probe of which the body 200 forms a part of. The body 200 for instance may comprise a flex foil comprising a plurality of conductive tracks 232 that extend onto the body edge(s) 220 by means of the body contact portions 230. A particular advantage associated of using such a novel flex foil is that the tip of the ultrasound probe may be manufactured in an innovative manner.

State of the art solutions wrap the flex foil around the IC die 100, after which interconnects between the IC die 100 and the flex foil are formed typically using bond wires extending from a bond pad 120 to a side surface of the flex foil, typically the outer surface of the flex foil. In addition to the previously explained drawback of these bond wires being relatively fragile and requiring a minimum pitch that causes the forward facing sensing surface, i.e. the ultrasound sensing area 110, to be covered by a relatively thick lens material, the wrapping of the flex foil around the IC die 100 usually does not result in the flex foil conforming particularly well to the shape of the IC die 100 as defined by the edge(s) 102.

For instance, in case of a circular IC die 100, a flex foil wrapped around the edge 102 of the IC die typically results in a creased flex foil, i.e. a flex foil comprising a plurality of folds extending in a length direction of the ultrasound probe, e.g. an ultrasonic catheter. This therefore increases the external diameter of the ultrasound probe, e.g. catheter, which can prohibit the use of the catheter in application domains where ultrathin catheters are required, e.g. diagnostic imaging of narrow parts of the human body such as arteries, veins, parts of the heart muscle and so on.

The combination of an IC die 100 comprising an ultrasound sensing area 110 and contact plates 130 with a flexible body 200, e.g. including a flex foil or another suitable flexible structure carrying body contact portions 230 on the edge(s) 220 of the flexible body 200 facilitates the formation of a more compact ultrasonic transducer because the flexible body 200 can be pre-formed prior to mounting the IC die 100 on the body 200, such that the opening 210 closely matches the dimensions of the IC die 100 as delimited by the edge(s) 102. In other words, the flexible body 200 may be shaped in such a manner that the IC die 100 tightly fits in the opening or recess 210.

FIGS. 8A-8F schematically depict a method for preforming a body 200 including a flex foil for receiving a circular IC die 100 comprising contact plates 130. In step FIG. 8A, a flex foil 201 forming part of the body 200 is provided. In an embodiment, the flex foil 201 is T-shaped including a first portion 202 including body contact portions 230 (not shown in FIG. 8A) on the upper edge 203 of the first portion 202. The body contact portions 230 for instance may be formed using plating techniques as previously explained.

The first portion 202 is to be formed into an annular section for receiving the IC die 100. The second portion 204 is to be formed into an arcuate section, e.g. a C-shaped section, in which a printed circuit board (PCB) carrying signal processing circuitry may be housed. By providing an arcuate (open) section 204, contacts between the PCB and the flex foil 201 may be easily established. The flex foil 201 typically comprises a plurality of conductive tracks 232 (not shown in FIG. 8A) extending from the body contact portions 230 to one or more side edges 205 of the flex foil 201 (or to the bottom edge 206) for establishing contacts with the PCB, e.g. through bond wires or any other suitable interconnect structure.

Figure 8A:
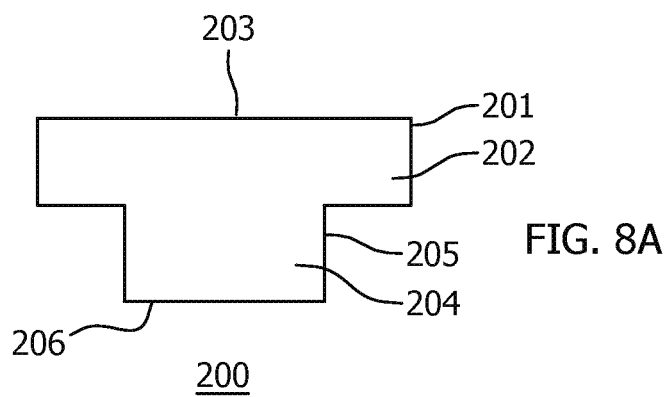
FIGS. 8A-8F schematically depict a method for forming a tip of an ultrasound probe according to an embodiment of the present invention.
Figure 8B:
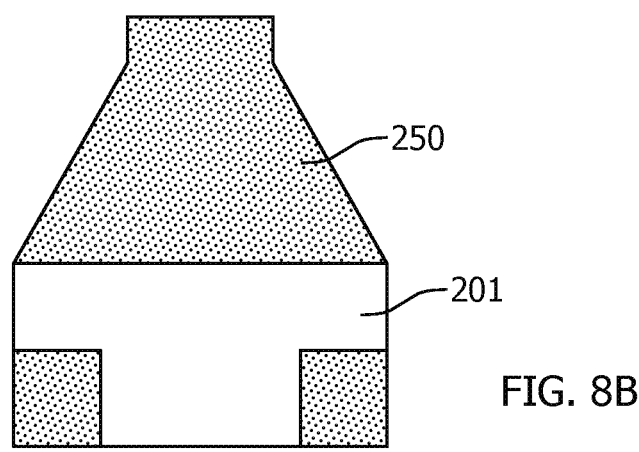

In step FIG. 8B, the flex foil 201 may be mounted on an adhesive flexible support 250, which preferably is made of an electrically insulating material, e.g. a polymer such as polyimide. The flexible support 250 may have rectangular section supporting the flex foil 201 and a tapered section extending from the rectangular section to facilitate the pre-shaping of the flex foil 201 and the flexible support 250. The overall shape of the adhesive flexible support 250 may be Y-shaped.

Next, a guide member 500 having a frustoconical cavity 510 extending between opposing surfaces of the guide member 500 is provided. In other words, the frustoconical cavity 510 has a relatively wide opening in one surface of the guide member 500 and a relatively narrow opening in the opposing surface of the guide member 500. The guide member 500 may be made of any suitable material, e.g. a metal, plastics and so on. An alignment pin 520 is provided that has an outer dimension such that it fits through the relatively narrow opening of the frustoconical cavity 510.

Figure 8C:
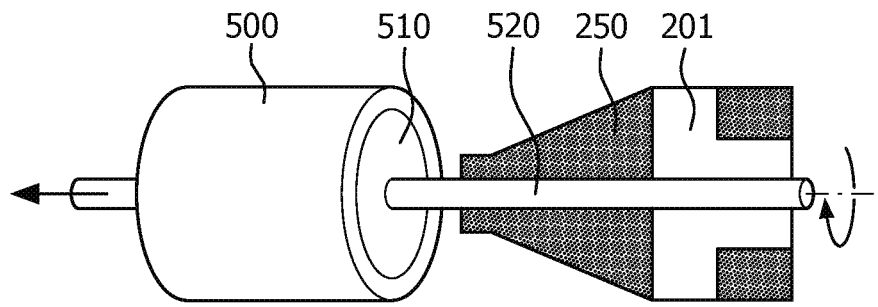

As demonstrated by the curved arrow in step FIG. 8C, the flex foil 201 supported by the adhesive flexible support 250 is rolled around a portion of the alignment pin 520 facing the relatively wide opening of the frustoconical cavity 510, after which part of the alignment pin 520 including the rolled flex foil 201 and adhesive flexible support 250 are pulled through the frustoconical cavity 510 as indicated by the straight arrow in step (c) such that the inner surface of the relatively narrow opening of the frustoconical cavity 510 is lined with the rolled flex foil 201 supported by the adhesive flexible support 250.

At this point it is noted that this narrow opening may form part of a cylindrical portion of the frustoconical cavity 510, which cylindrical portion has a length 1 corresponding to the desired length of the body 200 when used as a tip in an ultrasound probe, e.g. an ultrasound probe and an inner diameter d that corresponds to the desired outer diameter of the body 200 when used as a tip in such an ultrasound probe.

Figure 8D:
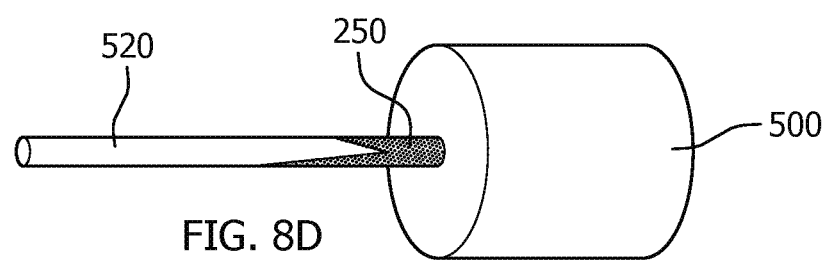
Figure 8E:
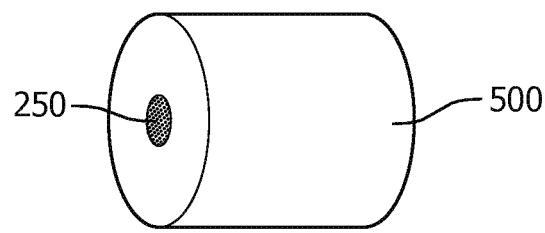

The resulting structure is shown in step FIG. 8D, which schematically depicts the alignment pin 520 after it has been partially pulled through the guide member 500. The excess adhesive flexible support 250, i.e. the tapered portion thereof, is removed from the alignment pin 520, e.g. through cutting after which the alignment pin 520 is removed from the guide member 500, thus leaving the cylindrical portion of the frustoconical cavity 510 lined with the flex foil 201 supported by the flexible support 250, as shown in step (e). Although not explicitly shown, it will be appreciated that the body contact portions 230 are exposed on the exposed edge of the flex foil 201 supported by the flexible support 250.

Figure 8F:
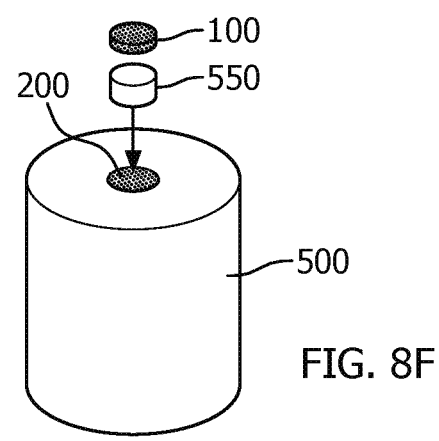

This structure may be used to mount an IC die 100 onto the exposed edge of the flex foil 201 supported by the flexible support 250, as is shown in step FIG. 8F. A backing member 550 may optionally be used to temporarily support the IC die 100 during the mounting process, e.g. to provide additional stability to the IC die 100 during the formation of interconnections between the contact surface portions 132 of the contact plates 130 and the body contact portions 230 on the edge 220 of the flex foil 201, which interconnections may be formed in any suitable manner, e.g. through soldering or gluing as previously mentioned. The backing member 550 may be removed upon completion of these interconnections, after which the body 200 including the IC die 100 may be removed from the guide member 500.

Alternatively, the backing member 550 may be affixed to the IC die 100, e.g. by inserting a layer of adhesive into the body 200 on the backing member 550 prior to inserting the IC die 100 into the body 200. In this embodiment, guide member 500 preferably is of a material having poor affinity with the adhesive, i.e. the adhesive does not adhere well to the material of the guide member 500 to facilitate the release of the body 200/backing member 550/IC die 100 assembly from the guide member 500, e.g. after curing the adhesive.

The body 200/backing member 550/IC die 100 assembly may be released from the guide member 500 by pressing against the backing member 550 through opening 510. The inclusion of the backing member 550 at the backside of the IC die 100 may for instance be advantageous to absorb sound waves travelling through the IC die 100 when in the tip of the ultrasound probe. The tip of the ultrasound probe may subsequently be completed by placement of a PCB in the arcuate section 204 of the body 200 including the flex foil 201 and connecting the PCB contacts to the conductive tracks 232 of the flex foil 201. As this is well-known per se, this will not be explained in further detail for the sake of brevity.

Figure 9:
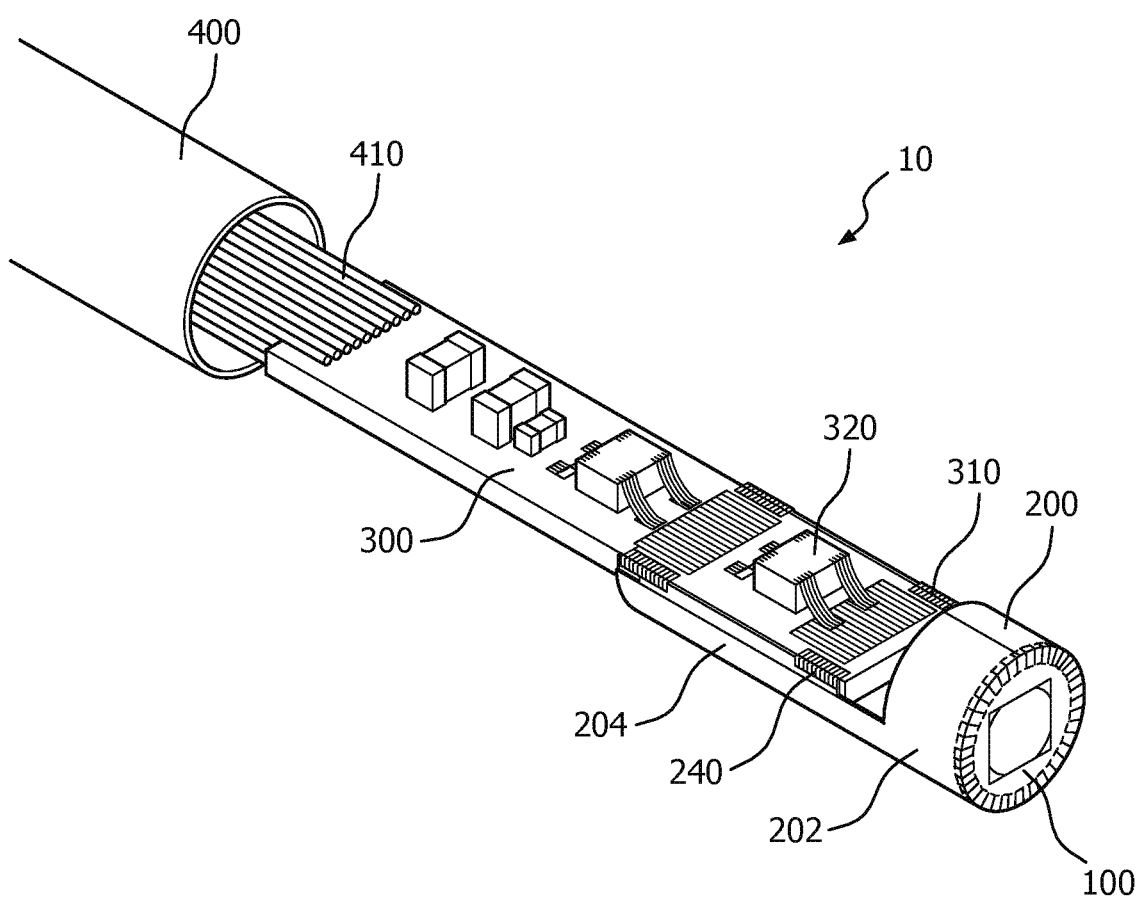
FIG. 9 schematically depicts a perspective view of an aspect of an ultrasound probe according to an embodiment of the present invention.

A non-limiting example of such a forward-looking ultrasound probe is schematically shown in FIG. 9. The forward-looking ultrasound probe 10, here a catheter, comprises the body 200 (including the supported flex foil 201) onto which the IC die 100 is mounted as previously described, i.e. by having the contact plates 130 of the IC die 100 contacting body contact portions 230 on the edge 220 of the flex foil 201. The body 200 may define a flexible tip of the ultrasound probe 10. The annular section 202 of the body 200 houses the IC die 100 whereas the arcuate section 204 of the body 200 houses part of a PCB 300 having board contacts 310 that are conductively coupled to the conductive tracks 230 (not shown in FIG. 9) of the body 200 by interconnections 240, e.g. bond wires or the like. To this end, the conductive tracks 230 typically comprise portions that act as electrically conductive second further contact surfaces for forming the interconnections with the PCB contacts 310.

The PCB 300 is typically connected at a section opposite the body 200 to conductive wires 410, e.g. a coaxial cable, which conductive wires 410 for instance may connect the PCB 300 to an external data processor and/or control unit (not shown), as will be explained in more detail below. The conductive wires 410, e.g. the coaxial cable, may be housed in a main body 400, e.g. a fibre or the like, onto which the tip of the ultrasound probe 10 is mounted.

The PCB 300 may comprise some signal processing circuitry 320, such as for instance a microbeam former as will be explained in more detail below. The tip of the ultrasound probe 10 may be covered in an electrically insulating protective material, e.g. a suitable resin, to protect the PCB 300 and the conductive parts of the tip to exposure to external environments, e.g. (corrosive) bodily fluids during use of the ultrasound probe 10. As this is entirely routine, it suffices to say that any suitable protective material may be used for this purpose. Such materials are readily available to the skilled person.

Figure 10:
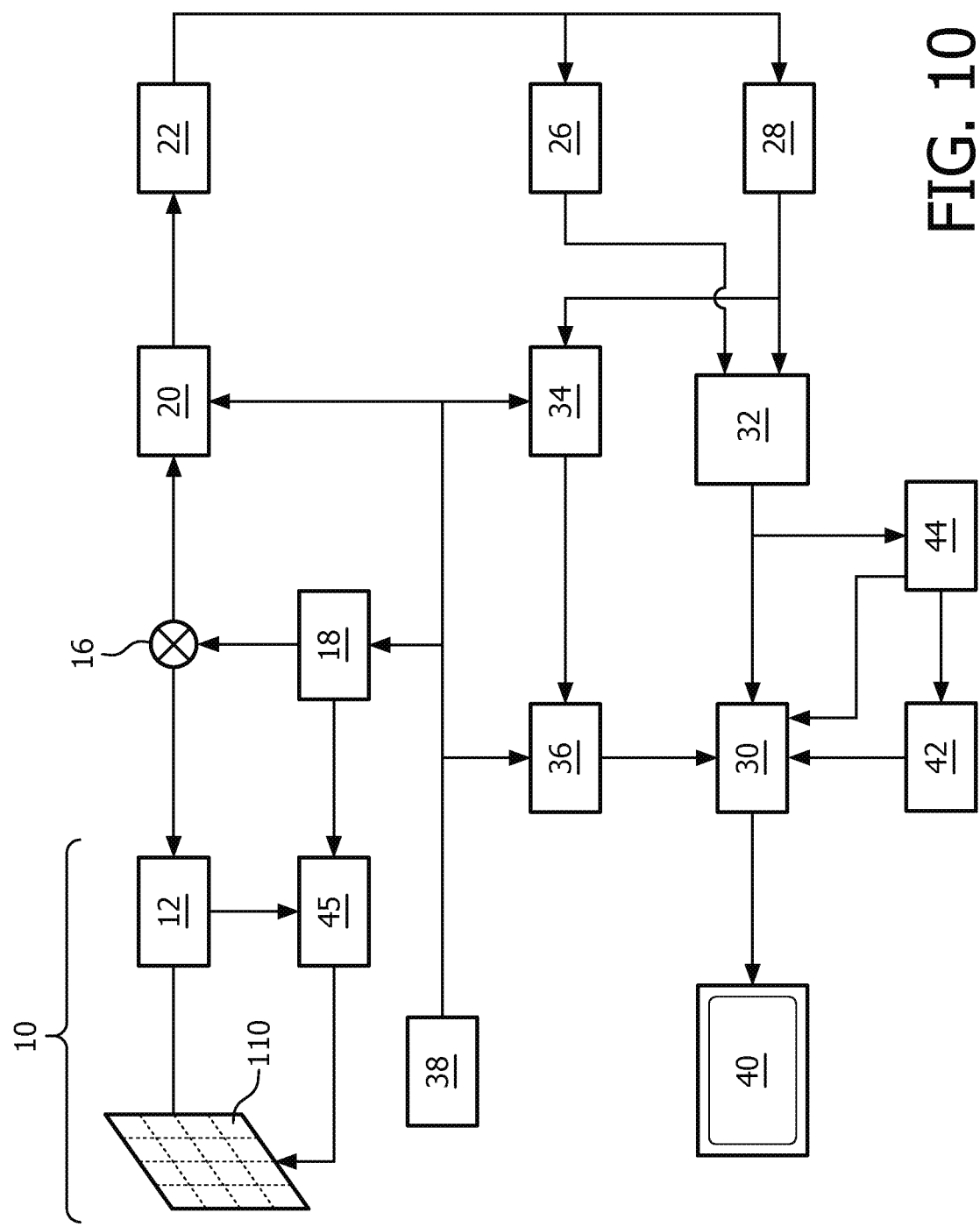
FIG. 10 schematically depicts a non-limiting example of an ultrasonic diagnostic system including an ultrasound probe according to an embodiment of the present invention.

Referring to FIG. 10, an example embodiment of an ultrasonic diagnostic imaging system with an array transducer probe according to an embodiment of the present invention is shown in block diagram form. In FIG. 10 a CMUT transducer array 110 on an IC die 100 (not shown in FIG. 10) is provided in an ultrasound probe 10 for transmitting ultrasonic waves and receiving echo information. The transducer array 110 may alternatively comprise piezoelectric transducer elements formed of materials such as lead zirconate titanate (PZT) or polyvinylidenefluoride (PVDF). The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells or piezoelectric elements. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial cable 410, to a transmit/receive (T/R) switch 16 which switches between transmission and reception and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control a DC bias control 45 for the CMUT array 1100. For instance, the DC bias control 45 sets DC bias voltage(s) that are applied to the CMUT cells 150 of a CMUT array 110.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 150 (see FIG. 2) or piezoelectric elements. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name.

The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound probe comprising a tip including:
   an integrated circuit die having a major surface delimited by at least one edge of the IC die, said major surface comprising an ultrasound sensing area and carrying a plurality of electrically conductive contact plates for suspending the IC die in a cavity; and
   a body having at least one further edge delimiting the cavity comprising the IC die, said at least one further edge comprising a plurality of electrically conductive first further contact surface portion, wherein the contact plates extending from said die major surface beyond the at least one edge such that each contact plate includes an exposed contact surface portion delimited by the at least one edge for mating with the electrically conductive further contact surface portion on the further edge of the body, said at least one further edge delimiting the cavity for receiving the IC die; and wherein each electrically conductive first further contact surface is conductively coupled to the contact surface portion of one of said contact plates.

2. The ultrasound probe of claim 1, wherein the ultrasound sensing area is defined by a plurality of capacitive micro-machined ultrasonic transducer elements.

3. The ultrasound probe of claim 1, wherein said major surface comprises a plurality of bond pads, and wherein each electrically conductive contact plate extends from one of said bond pads.

4. The ultrasound probe of claim 1, wherein the electrically conductive contact plates are made of a metal or metal alloy.

5. The ultrasound probe of claim 4, wherein the metal or metal alloy is diamagnetic.

6. The ultrasound probe of claim 1, wherein the contact plates have a thickness of at least 20 micron.

7. The ultrasound probe of claim 1, wherein each electrically conductive first further contact surface is conductively coupled to the contact surface portion of one of said contact plates by a conductive solder or a conductive glue.

8. The ultrasound probe of claim 1, wherein said body comprises a flex foil including a plurality of conductive tracks on the flex foil, wherein each conductive track includes one of said first further contact surfaces.

9. The ultrasound probe of claim 1, wherein:
   said tip further houses signal processing circuitry on a printed circuit board carrying a plurality of board contacts conductively coupled to signal processing circuitry inputs;
   the flex foil comprises an annular section housing the IC die and an arcuate section extending from the annular section, said arcuate section comprising a pair of opposing edge portions each comprising a plurality of electrically conductive second further contact surfaces, each electrically conductive second further contact surface forming part of one of said conductive tracks; and
   each electrically conductive second further contact surface is conductively coupled to one of said board contacts.

10. An ultrasonic diagnostic system including the ultrasound probe of claim 1.

* * * * *